US010322246B2

(12) United States Patent
Morlok et al.

(10) Patent No.: US 10,322,246 B2
(45) Date of Patent: Jun. 18, 2019

(54) INJECTION DEVICE WITH TOOTHED GEARING

(71) Applicant: H & B ELECTRONIC GMBH & CO. KG, Deckenpfronn (DE)

(72) Inventors: Tobias Morlok, Mötzingen (DE); Wilfried Weber, Schopfloch (DE)

(73) Assignee: H & B ELECTRONIC GMBH & CO. KG, Deckenpfronn (DE)

( * ) Notice: Subject to any disclaimer, the term of this patent is extended or adjusted under 35 U.S.C. 154(b) by 144 days.

(21) Appl. No.: 15/314,415

(22) PCT Filed: Apr. 27, 2015

(86) PCT No.: PCT/EP2015/000863
§ 371 (c)(1),
(2) Date: Dec. 5, 2016

(87) PCT Pub. No.: WO2015/185176
PCT Pub. Date: Dec. 10, 2015

(65) Prior Publication Data
US 2017/0197038 A1 Jul. 13, 2017

(30) Foreign Application Priority Data
Jun. 3, 2014 (DE) .................... 20 2014 004 561 U

(51) Int. Cl.
*A61M 5/31* (2006.01)
*A61M 5/315* (2006.01)
*A61M 5/32* (2006.01)
*A61M 5/46* (2006.01)
*A61M 5/20* (2006.01)

(52) U.S. Cl.
CPC ........ *A61M 5/31591* (2013.01); *A61M 5/321* (2013.01); *A61M 5/322* (2013.01);
(Continued)

(58) Field of Classification Search
CPC .... A61M 5/31591; A61M 5/322; A61M 5/46; A61M 5/3243; A61M 5/321;
(Continued)

(56) References Cited

U.S. PATENT DOCUMENTS 4,231,368 A * 11/1980 Becker .................... A61M 5/20
604/117
6,454,743 B1    9/2002 Weber
(Continued)

FOREIGN PATENT DOCUMENTS

DE     78 08 802 U1    8/1979
DE    203 11 996 U1   10/2003
(Continued)

*Primary Examiner* — Amber R Stiles
(74) *Attorney, Agent, or Firm* — Birch, Stewart, Kolasch & Birch, LLP

(57) ABSTRACT

An injection device has a housing in which a syringe can be received that has an injection needle, a receiving chamber, a piston and a piston ram, and a control arrangement for controlled actuation of the syringe during an application procedure that includes at least one puncture stroke, one injection stroke and one return stroke. The control arrangement has an actuation element for applying a drive force to a syringe holder which is movable relative to the housing and on which the receiving chamber can be secured, a ram holder which is movable relative to the housing and on which the piston ram can be secured, and a transmission mechanism by means of which the ram holder can be coupled to the actuation element. Provision is made that the transmission mechanism has a toothed gearing by means of which the ram holder can be driven, according to a relative movement of the actuation element with respect to the housing, and which for this purpose has teeth on the housing.

17 Claims, 18 Drawing Sheets

Figure 1:
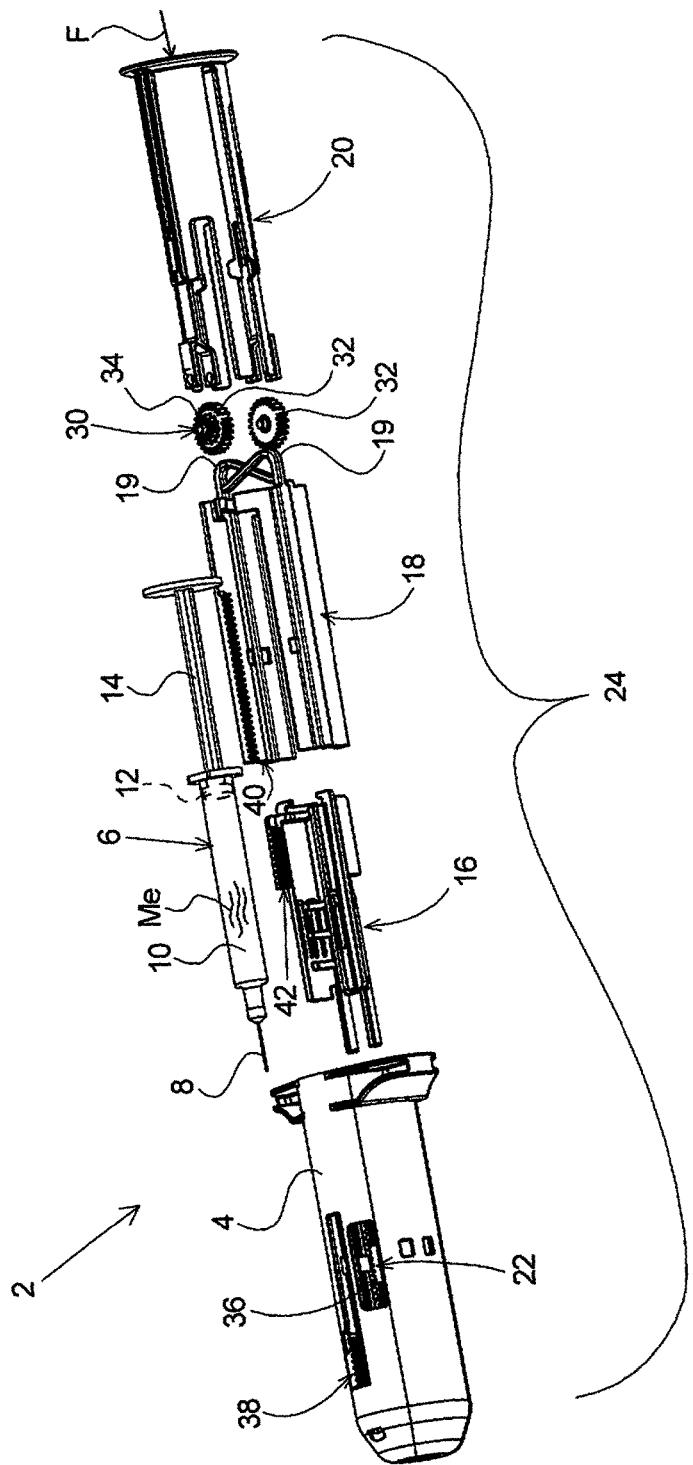

(52) U.S. Cl.
CPC ............ *A61M 5/3243* (2013.01); *A61M 5/46* (2013.01); *A61M 2005/206* (2013.01); *A61M 2005/3143* (2013.01); *A61M 2005/3152* (2013.01); *A61M 2005/3247* (2013.01)

(58) Field of Classification Search
CPC .. A61M 2005/3247; A61M 2005/3152; A61M 2005/3143; A61M 2005/206
See application file for complete search history.

(56) References Cited

U.S. PATENT DOCUMENTS

| | | |
|---|---|---|
| 8,603,043 B2 | 12/2013 | Chevalier |
| 9,061,103 B2 | 6/2015 | Kemp et al. |
| 2001/0047151 A1* | 11/2001 | Xian ................. A61B 17/3401 604/117 |
| 2006/0258990 A1 | 11/2006 | Weber |
| 2008/0188798 A1 | 8/2008 | Weber |
| 2011/0028910 A1 | 2/2011 | Weber |
| 2012/0056019 A1 | 3/2012 | Renz et al. |

FOREIGN PATENT DOCUMENTS

| | | | |
|---|---|---|---|
| DE | 20 2005 014 958 U1 | 12/2005 | |
| DE | 20 2009 003 009 U1 | 6/2009 | |
| FR | 2 767 479 A1 | 2/1999 | |
| FR | 2767479 A1 * | 2/1999 | ............ A61M 5/315 |
| JP | 2014-502887 A | 2/2014 | |
| WO | WO 99/56805 A1 | 11/1999 | |
| WO | WO 2012/085032 A1 | 8/2012 | |

* cited by examiner

INJECTION DEVICE WITH TOOTHED GEARING

The invention relates to an injection device for simplified administration of a medication from a syringe according to the preamble of claim 1. The injection device either comprises a housing, in which the syringe is firmly received, wherein the housing can be disposed of together with the syringe, in particular after single use thereof, or the housing is formed such that the syringe can be received therein in such a way that the syringe can be removed after use and later replaced by a new syringe. In either case the syringe comprises an injection needle, a receiving chamber for the respective medication, a piston and a piston ram. The injection device also comprises a control arrangement, by means of which the syringe can be actuated in a controlled manner during an application procedure which comprises at least a puncture stroke, an injection stroke and a return stroke. The control arrangement comprises an actuation element on which a drive force generated manually, electrically or by a mechanical force accumulator can be applied. The control arrangement further comprises a syringe holder that can move relative to the housing, on which the receiving chamber of the syringe can be secured, and a ram holder which can move relative to the housing, on which the piston ram of the syringe can be secured. Further, a transmission mechanism is provided, by means of which the ram holder can be coupled with the actuation element and/or the movement thereof.

Such injection devices enable a particularly simple administration of medications for treating a wide variety of diseases by means of a syringe, wherein the administration can be undertaken in particular by the patients themselves. Examples of such diseases and uses are thrombosis prevention, diabetes, cancer therapy, arthritis, multiple sclerosis, etc. The medications are generally administered subcutaneously, i.e. in the subcutaneous fatty tissue.

A large number of so-called safety syringes are available on the market, which can be operated by the patients themselves and, after use, can be safely disposed of with a needle cover. Such a safety syringe is found, for example, in U.S. Pat. No. 8,603,043 B2.

However, the disadvantage of the known disposable syringes is that the needle is visible before the injection and thus also presents a risk of injury. Moreover it is difficult for persons having a needle phobia to use such syringes. For some known disposable syringes, there is the further disadvantage that, after an injection has been performed, the patient must first withdraw the needle or the syringe before the needle protection can be installed. The dwell time required for many applications must also be judged solely by the patient, which means that in many applications a sufficient dwell time, during which the needle remains in the tissue, is not maintained. It can therefore occur that the fluid pressure built up by the injected medication is not sufficiently dissipated, leading to discharge of the medication in the puncture channel.

A fully automatic injection device is known from DE 203 11 996 U1, by means of which, during an application procedure comprising a puncture stroke, an injection stroke, a dwell time and a return stroke, the syringe can be actuated in a controlled manner and for which the above-mentioned disadvantages do not therefore occur. The control arrangement used in this case however requires a certain degree of complexity, which does not allow cost effective use of the injection device as a disposable injection device.

FR 2 767 479 A1 discloses an injection device comprising a housing, on which a two-stage gear wheel is rotatably mounted. A larger toothing of the gear wheel meshes with a piston ram which abuts a piston of a syringe, by means of which a medication received in the syringe can be injected. Simultaneously, a smaller toothing of the gear wheel meshes with a slider-shaped actuation element on which a tensile force or a compression force can be applied outside the housing, in order to move the gear wheel in a rotary motion via the small toothing and thus to displace the piston ram relative to the housing via the large toothing.

The problem addressed by the invention is that of avoiding the stated disadvantages for an injection device of the type in question, and providing a safe and user-friendly use with an inexpensive production.

Said problem is solved by an injection device having the features of claim 1. The transmission mechanism comprises a toothed gearing, by means of which the ram holder can be driven depending on a relative movement of the actuation element relative to the housing. For this purpose, the toothed gearing comprises a toothing on the housing itself, which is formed, for example, as a single piece with the housing or is mounted thereon. The use of a toothed gearing as an integral component of the transmission mechanism thus enables the control arrangement to be implemented with a very low number of components. In addition, the components required for the transmission mechanism or the control arrangement are produced, at least for the most part and preferably entirely, from a cost effective material such as, in particular, plastics. The use of the toothed gearing enables both high comfort of use and an accurate control function while the injection device can be produced relatively cost effectively, which in turn enables the use of the injection device as a disposable product.

In a particularly advantageous embodiment, the toothed gearing comprises a first actuation-element-side toothing, which can be brought into meshing engagement in the drive direction of the actuation element with a first housing-side toothing thus generating a first direction of rotation. Spaced apart therefrom, the first actuation-element-side toothing can also be brought into meshing engagement with a second housing-side toothing arranged on another side of the housing, thus generating a second direction of rotation, wherein the second direction of rotation is orientated opposite to the first direction of rotation. In this way it is possible, while applying the drive force to the actuation element in just one application direction, to generate, by means of the transmission mechanism, two mutually opposite movements of the syringe holder and/or of the ram holder. In this way, a particularly simple transformation of a puncture or injection stroke into a return stroke is possible.

It is advantageous if the toothed gearing comprises a gear wheel rotatably mounted on the actuation element, that can be brought into meshing engagement both with a housing-side toothing and with a ram-holder-side toothing. In this way, the drive force can be transferred in a particularly simple manner to the ram holder, depending on a relative movement of the actuation element with respect to the housing of the actuation element.

Advantageously, the gear wheel is also brought at least into meshing engagement with a syringe-holder-side toothing. In this way it is possible, by means of the drive force, to simultaneously drive the syringe holder and the ram holder and thus also move these in the specified relation to one another.

Further, it is advantageous if at least one second actuation-element-side toothing is provided on the gear wheel in addition to the first actuation-element-side toothing, and the first actuation-element-side toothing comprises a first number of teeth and the second actuation-element-side toothing comprises a second number of teeth, different from the first number of teeth. Through these at least two different number of teeth, it is possible via different movement sections of the actuation element, to generate different relative speeds between one or more movable components and the housing. Thus in the drive direction of the actuation element, both actuation-element-side toothings can be brought into meshing engagement with mating toothings, generating a rotary movement with different gearing ratios. In this way, the generation of a simultaneous movement relative to the housing of two movable parts, with each other and in a determined relation to one another, is possible.

It is also advantageous if the toothings and mating toothings are formed at least partially as pointed teeth, through which a blocking of the transmission mechanism due to toothing combs coming to lie exactly on top of one another can be avoided. In a further advantageous embodiment, the toothings and mating toothings are at least partially resiliently formed. In this way, a complete blocking of the control arrangement due to the toothing combs coming to lie on top of one another can be completely excluded, since in this case either the gear wheel held on the actuation element or the respective mating toothing is elastically displaced until the blocking is removed and a meshing engagement is produced. It is also advantageous if the housing-side toothings have tooth heights increasing, at least in regions, in the application direction. In this way, the actuation-element-side toothings can be brought in a particularly even and trouble-free manner, into meshing engagement with the respective mating toothings.

Advantageously, spring elements are provided on the ram holder, by means of which a pretension in the drive direction can be applied to the piston ram. Through said pretension, manufacturing tolerances of the housing and of the syringe, and/or tolerances related to the fill level of the syringe, can be compensated on the syringe holder or on the ram holder.

In addition, it is advantageous if at least one damping element is provided interacting with the actuation element, through which a simultaneous movement thereof and thus of the entire control arrangement can be ensured, in particular during a manual application of the actuation element.

Advantageously, a blocking element is also provided, by means of which the actuation element can be blocked in a starting position until a threshold value of a drive force acting in the drive direction is attained. It is thus ensured that the application process only starts if the operating person applies a sufficient driving force to the actuation element. In this way, it is also ensured that the application process proceeds at a sufficient speed.

It is advantageous if the blocking mechanism comprises a spring tab that can abut with a stop, through which a blocking of the actuation element up to the threshold value can be configured in a particularly simple manner. In an alternative embodiment, the blocking mechanism comprises a locking element that can be sheared off, wherein the blocking mechanism can be produced particularly cost effectively. In a further alternative embodiment, the blocking mechanism comprises a locking element that can be pivoted against a spring force. In this way, the injection device can be set, in a particularly simple manner, to different threshold values of the drive force through selection of corresponding spring elements. In a further alternative embodiment the blocking mechanism comprises a switchable gear wheel acting together with the actuation element, through which a drive speed of the actuation element can be particularly accurately determined when the threshold value of the drive force is exceeded. In a particularly advantageous embodiment, the syringe holder can be securely coupled to the ram holder for carrying out the puncture step. In this way, an impeding relative movement of the ram holder relative to the syringe holder during the puncture step can be excluded. It is particularly advantageous if the coupling can be produced by means of the first actuation-element-side toothing of the gear wheel, which for this purpose is simultaneously engaged with both a mating toothing of the syringe holder and of the ram holder. In this procedure, both holders require no special components for the coupling. Advantageously, the gear wheel can be displaced in order to remove the coupling between the syringe holder and the ram holder after the end of the puncture stroke, which enables a particularly simple decoupling. In this case, it is advantageous if the gear wheel is pivotably mounted, so that the time of the decoupling can be determined in a particularly simple manner, such as for example by a deflection means securely applied against the housing. Alternatively, it is advantageous if the gear wheel is displaceably mounted in the radial direction, wherein complete decoupling can be performed particularly quickly. In a further alternative embodiment, the syringe-holder-side toothing is displaceable between the syringe holder and the ram holder after completion of a puncture stroke in order to remove the coupling, wherein the gear wheel held on the actuation element can be particularly stably mounted, while the decoupling occurs simply through separation of the syringe-holder-side toothing.

In a further particularly advantageous embodiment, the coupling can be produced by means of an engagement element removably engaged in a holder. In this way, the coupling can also be made using simple means, independently of the meshing engagement of the gear wheels. Alternatively, the coupling can be produced by means of a displaceable sliding block, which enables a particularly cost-effective implementation of the coupling and uncoupling. In a further alternative embodiment, the coupling can be produced by means of a locking element that can be sheared off, which allows a particularly simple decoupling. In a further alternative embodiment, the coupling can be produced by means of a switchable freewheel, wherein the decoupling can occur without a noticeable expenditure of force on the part of the operator.

It is particularly advantageous if the toothed gearing is provided with an empty stroke to produce a dwell time, by means of which, despite the relative movement of the actuating element relative to the housing, no drive force can be transferred to the ram holder. In this way, through the use of the gear wheel as an essential part of the transmission mechanism, it is also possible to specify in advance the dwell time required for multiple applications, during which the needle remains in the tissue. In this way it can be ensured that the fluid pressure built up by the injected medication is sufficiently dissipated before removal of the syringe, resulting in no substantial discharge of the medication in the puncture channel.

Additionally, it is advantageous if, in order to perform the return stroke, the second actuation-element-side toothing of the gear wheel can be brought into meshing engagement with the second mating toothing that is formed by the housing-side toothing, and the first toothing gear wheel is simultaneously in meshing engagement with the ram-holder-side toothing, wherein in addition the syringe holder is securely coupled with the ram holder. This allows a precisely timed specified start of the return stroke to be attained, in particular in relation to the dwell time.

Advantageously, the coupling can thus be produced by means of the first toothing of the gear wheel, which in turn requires no additional elements for the coupling of the ram holder with the syringe holder. Alternatively, the coupling can be produced by means of a spring element removably engaged in a holder, through which the coupling between ram holder and syringe holder can occur independently of the toothed gearing.

In an advantageous embodiment, the actuation element can additionally be adjusted in an end position, in which the return stroke is completed and the needle is again arranged completely inside the housing. Thus, an in particular accidental new operation of the injection device, in which the needle again comes out of the housing and could thus lead to injuries, can be prevented. In this way, a safe disposal of the needle is enabled following a successful use of the injection device. The locking occurs advantageously by means of a catch held on the actuation element, which can abut on a catch stop in the end position. This allows the elements required for producing the locking mechanism to be produced in a particularly simple and cost effective manner.

In a particularly advantageous embodiment, the housing comprises an end-face-side housing part, which can be displaced with respect to the rest of the housing in order to set a puncture depth. This allows the injection device to be set by simple means for different forms of application. Here, it is advantageous if the end-face-side housing part is held movably on the rest of the housing, enabling rapid adjustment of the puncture depth over a relatively large adjustment range. Alternatively, the end-face-side housing part can be held on the rest of the housing by means of an adjustable screw connection, which enables a stable and continuous setting of each puncture depth required. In a further alternative embodiment, the end-face-side housing part is displaceable relative to the rest of the housing along a control cam, through which, in particular, different predetermined puncture depths can be particularly easily set. In a further alternative embodiment, the end-face-side housing part can be adjusted by means of a displaceable actuation element, which enables a particularly comfortable setting of different puncture depths. In a further alternative embodiment, the end-face-side housing part is respectively formed by one or more exchangeable spacers, mounted on the rest of the housing. By respective application of one of these spacers, a specified puncture depth can thus be set on the injection device.

In addition, it is particularly advantageous if the actuation element can be acted upon by a drive force via a mechanical force accumulator. In this way, the injection device can also be used by patients who are motor impaired and thus have problems in applying the required drive force to the actuation element during use of the injection device. Here, it is advantageous if the mechanical force accumulator has a constant force spring, through which the mechanical force accumulator can generate a particularly even drive force.

Figure 2:
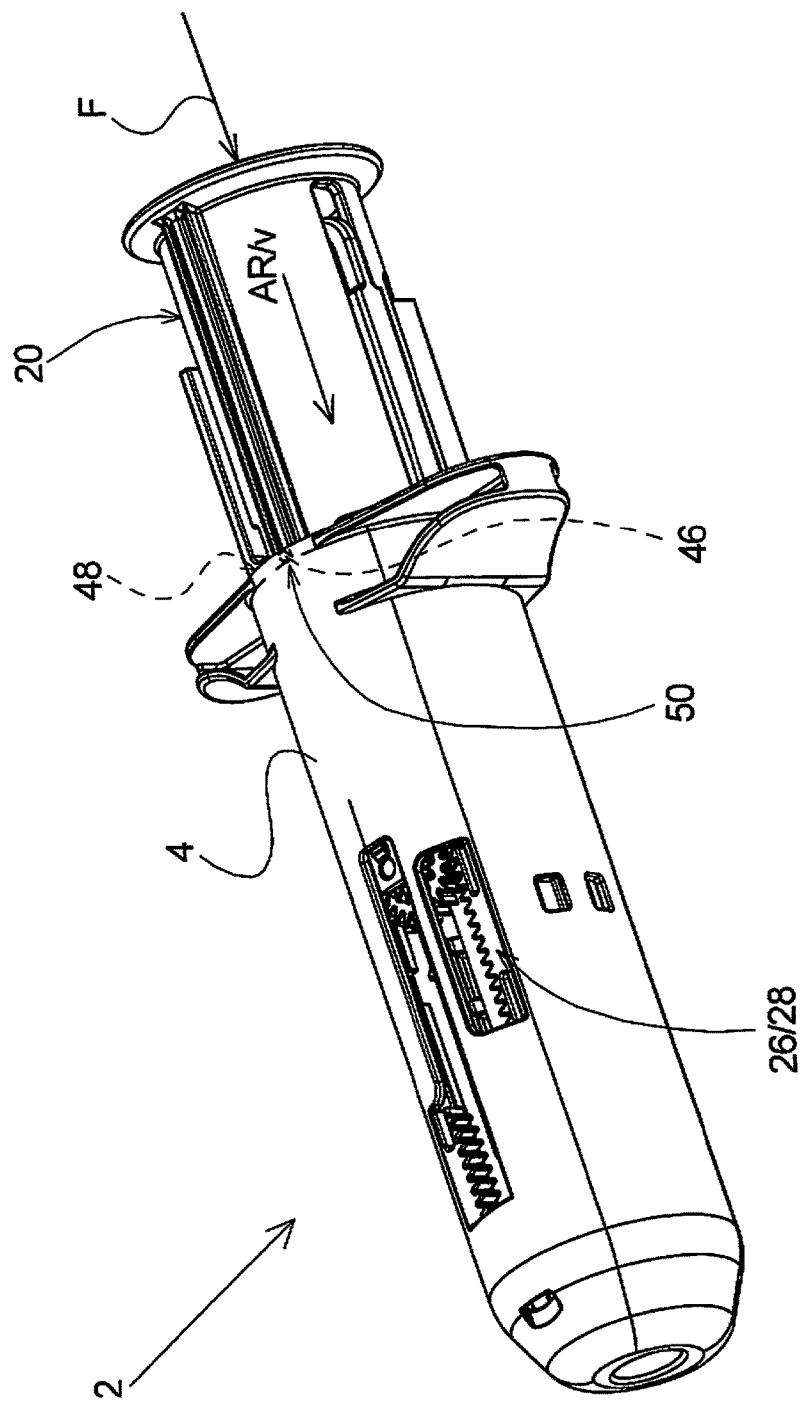
Figure 3:
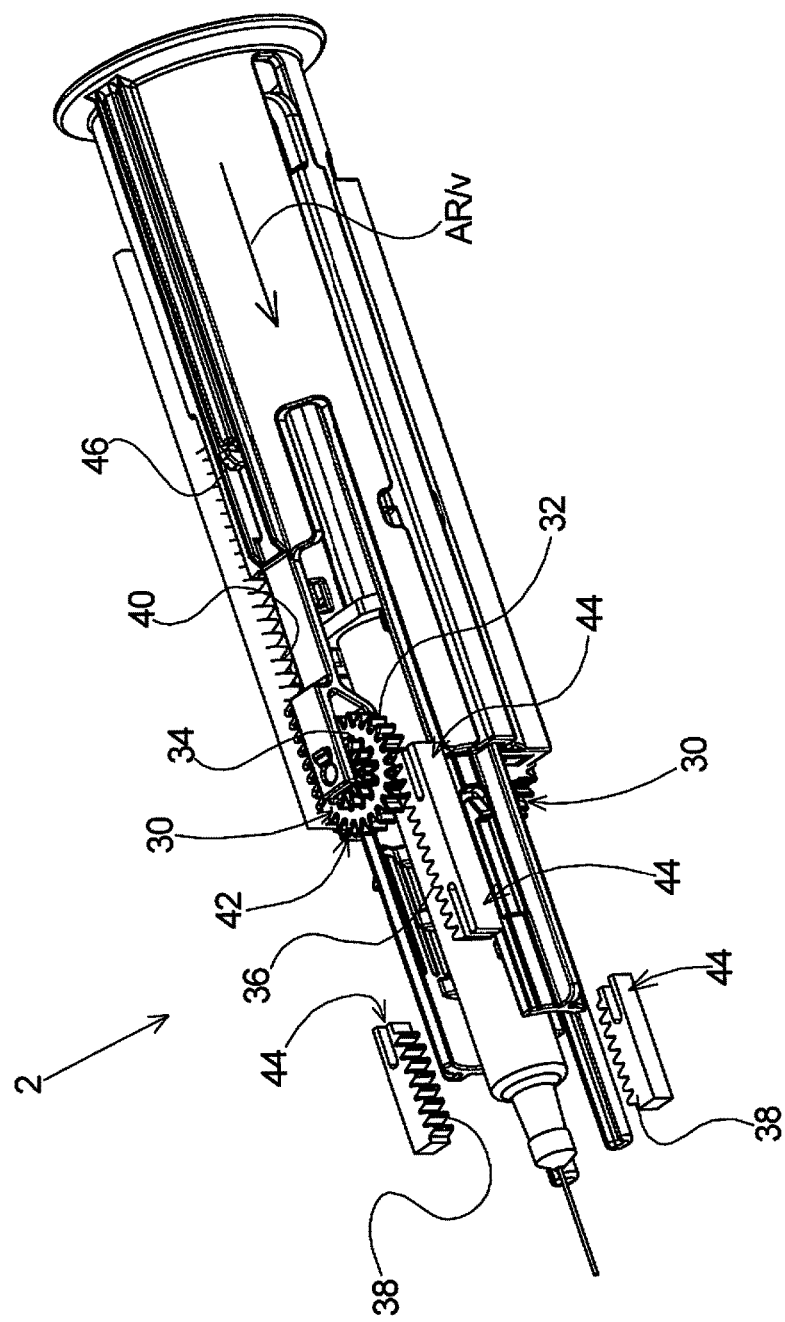
Figure 4:
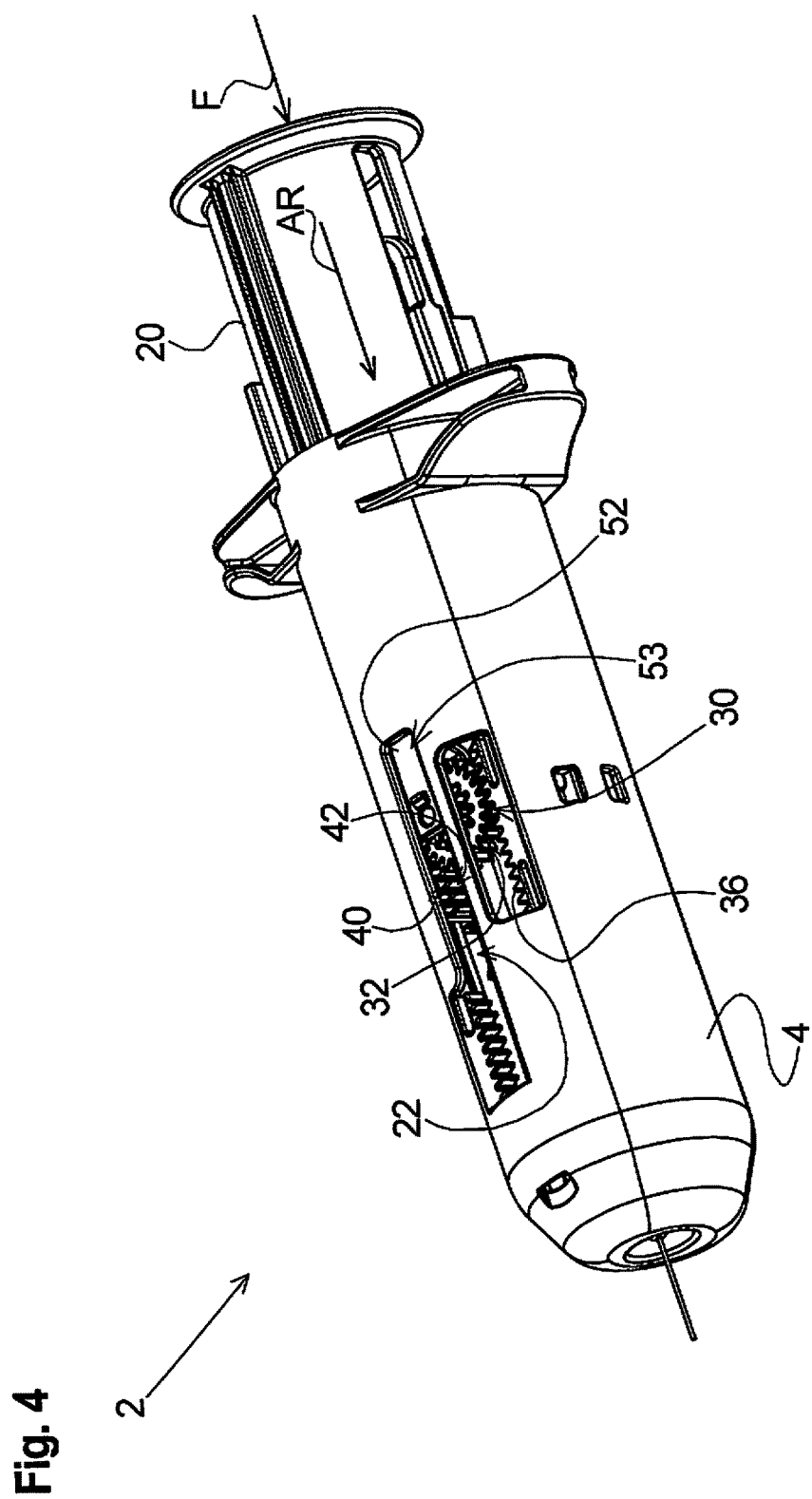
Figure 5:
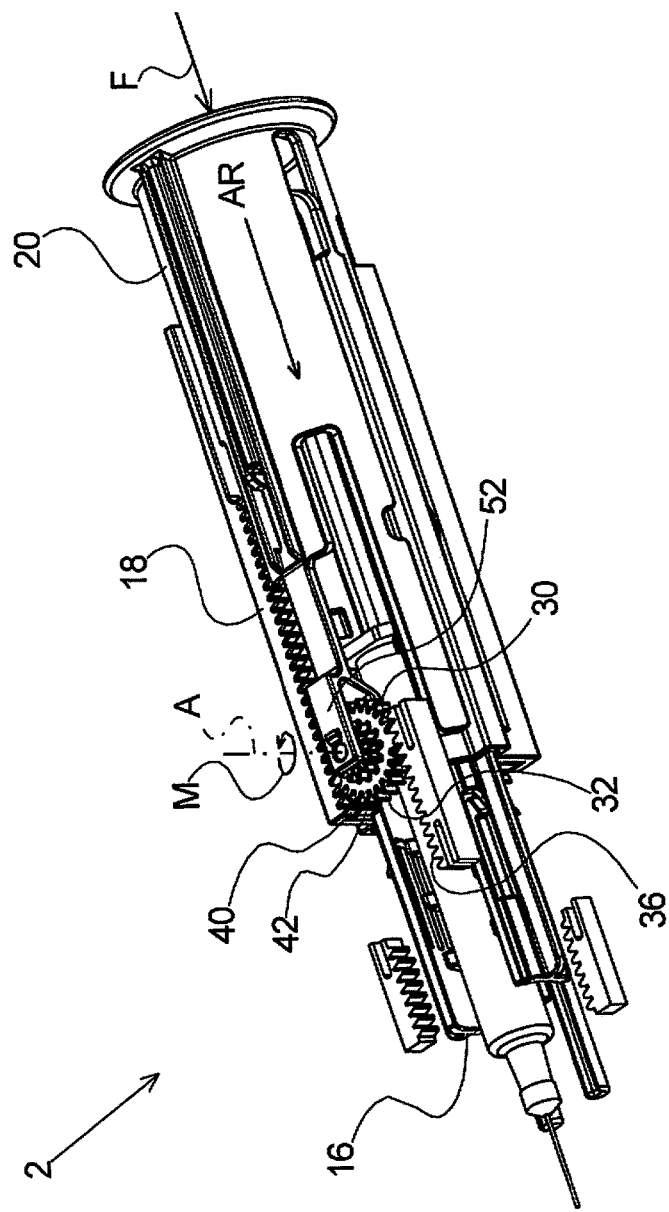
Figure 6:
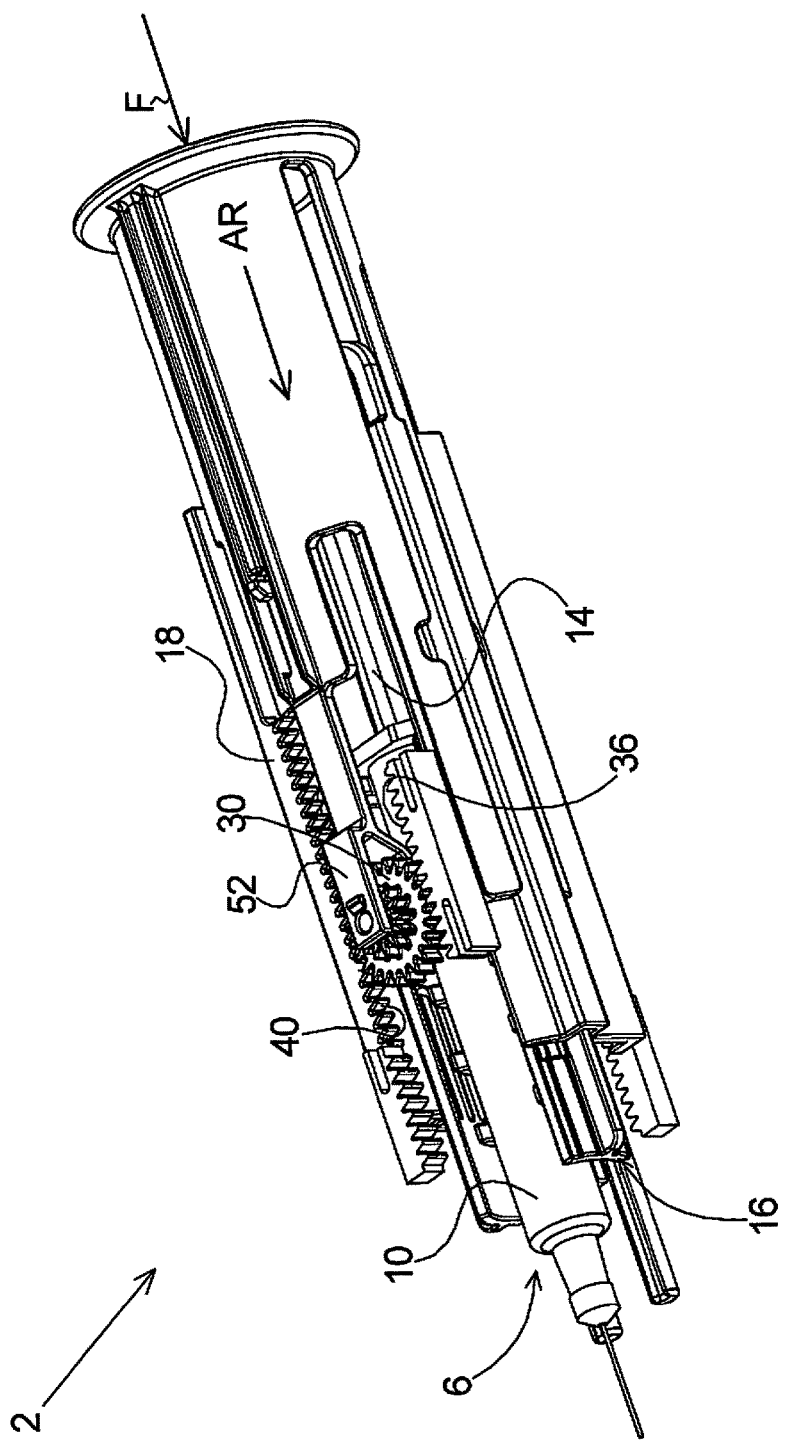
Figure 7:
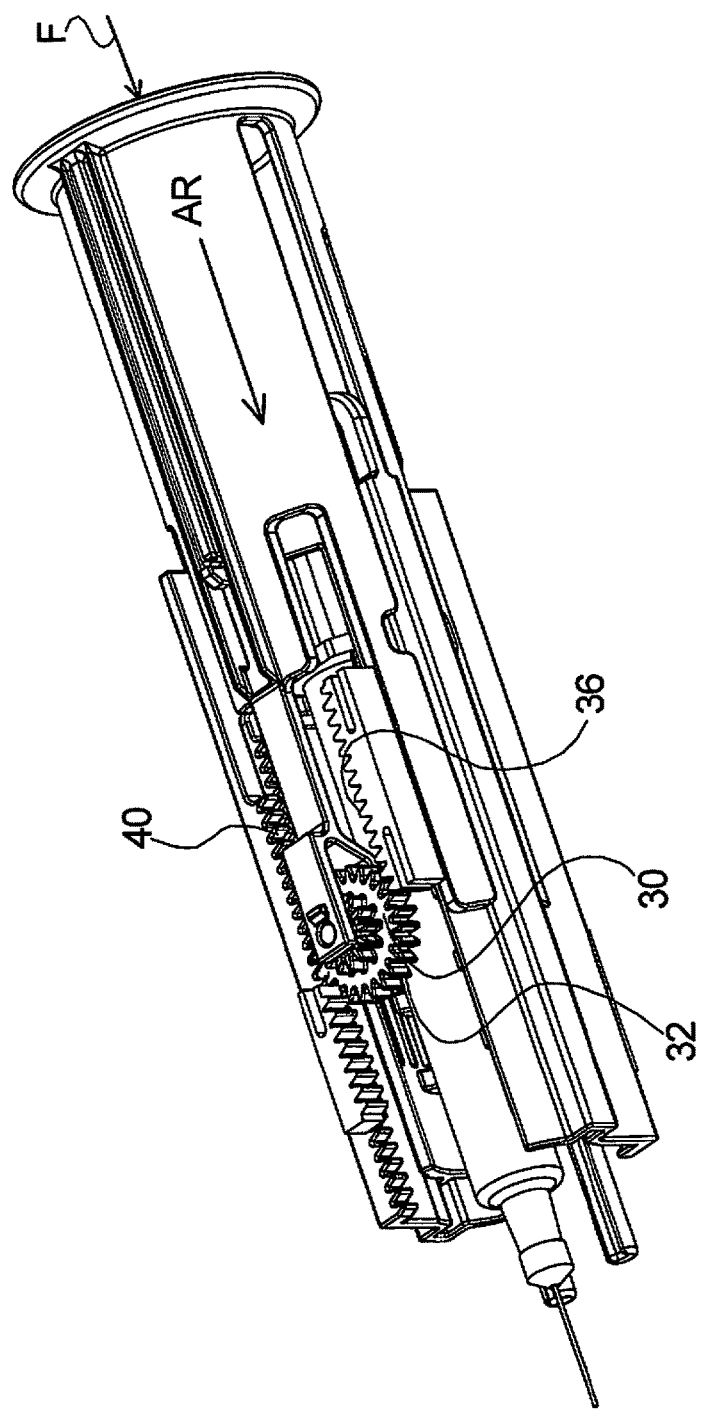
Figure 8:
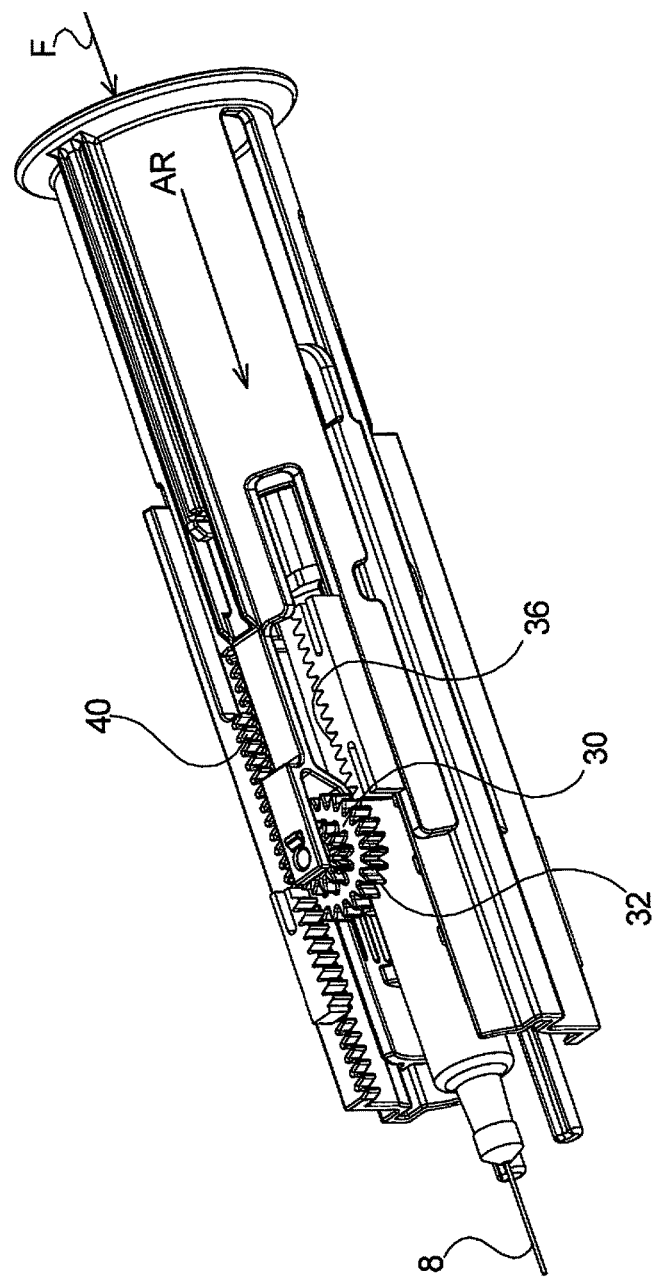
Figure 9:
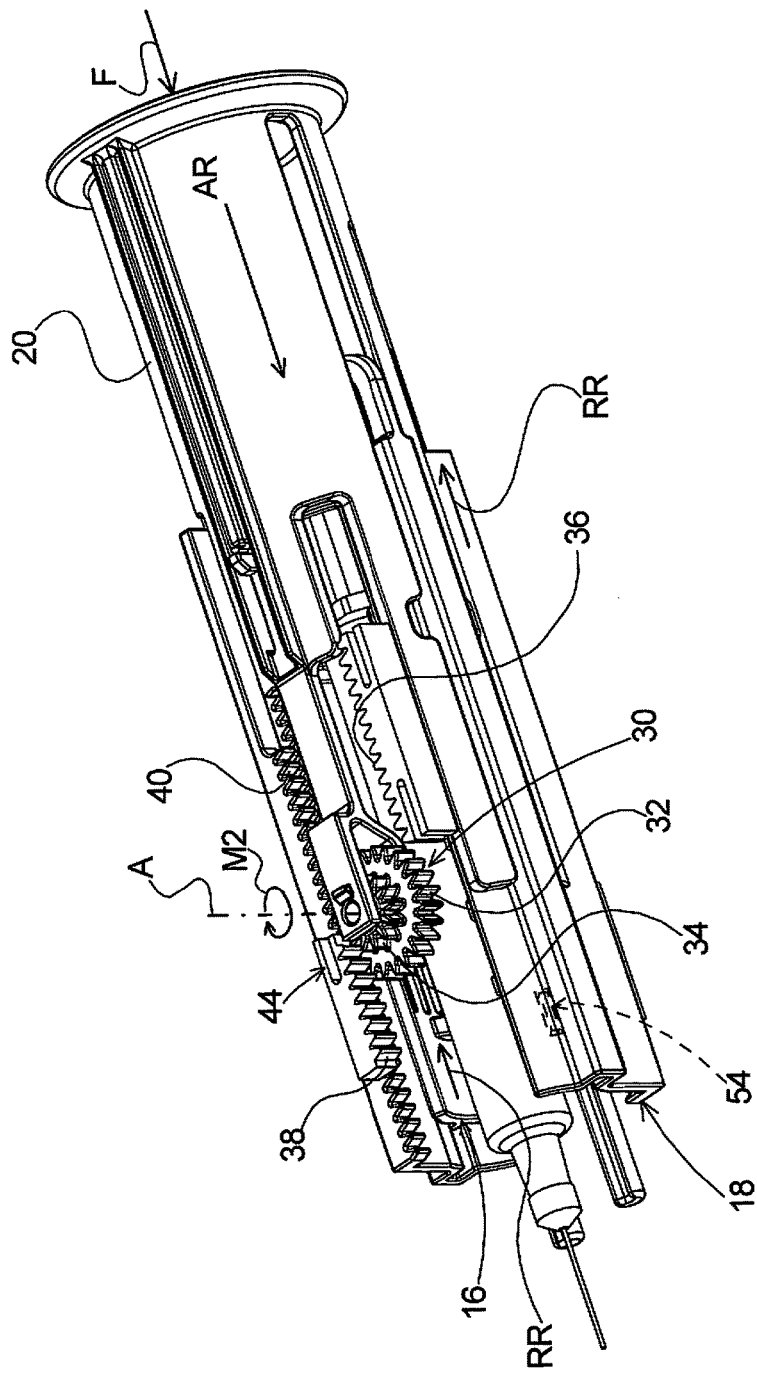
Figure 10:
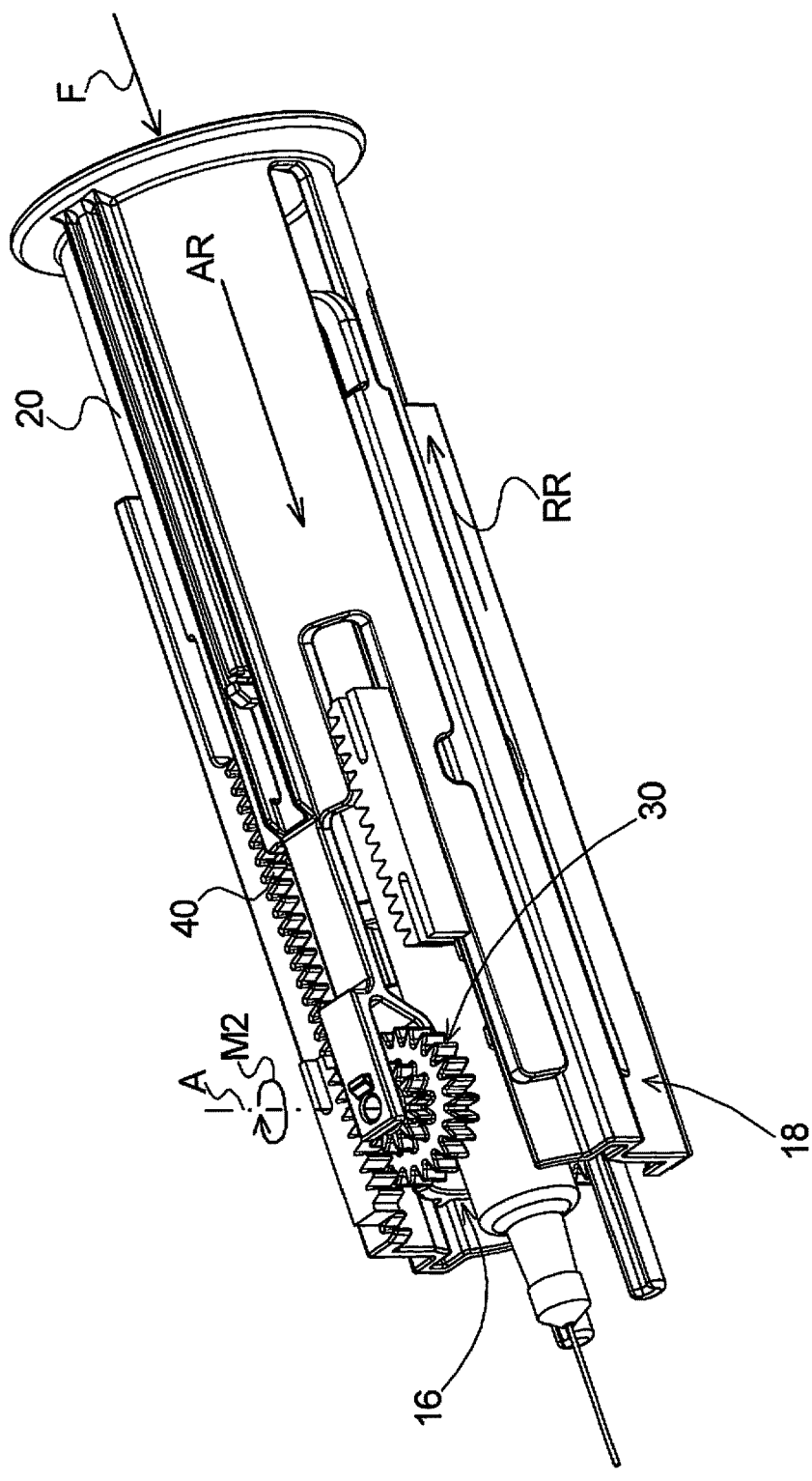
Figure 11:
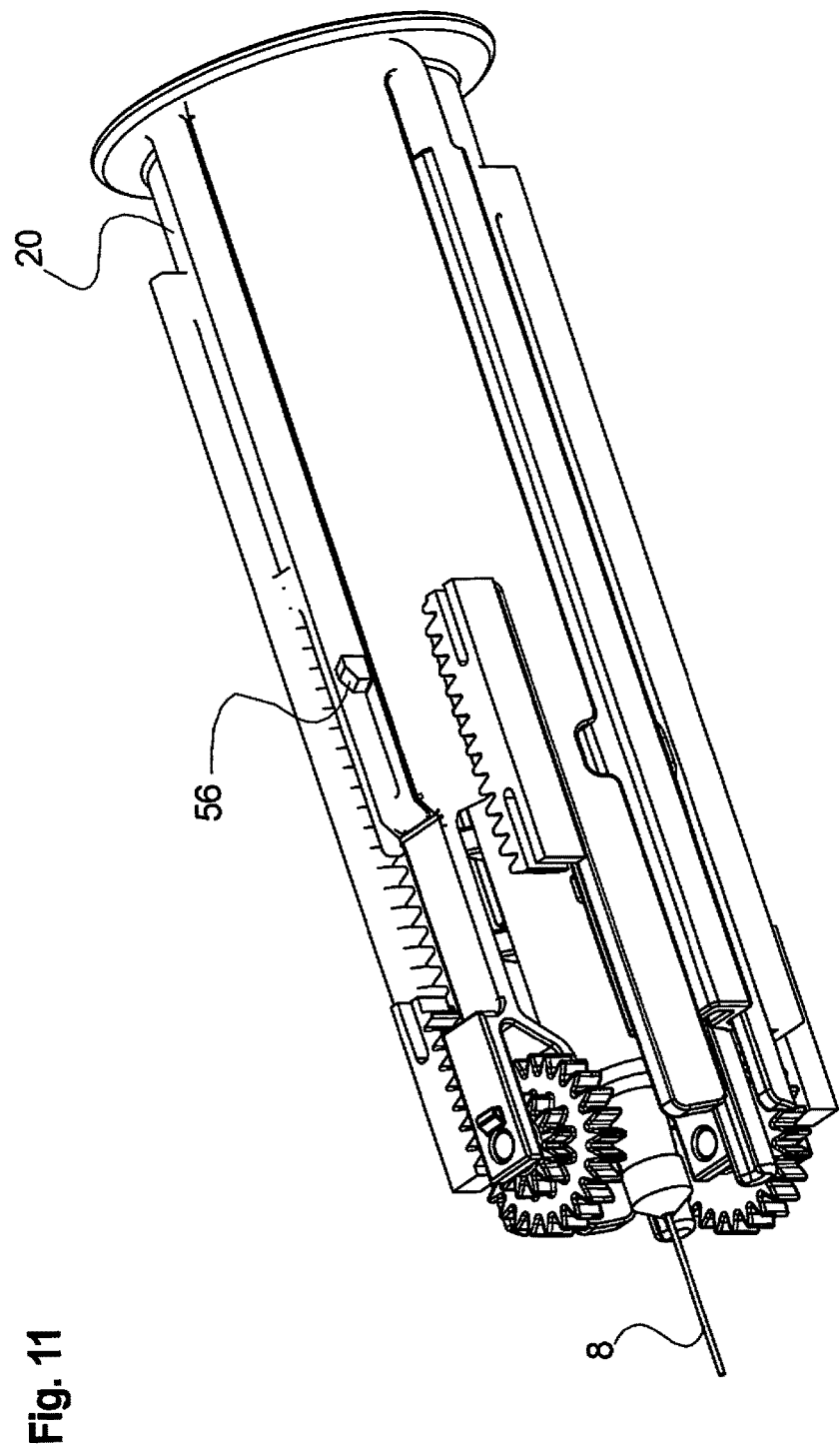
Figure 12:
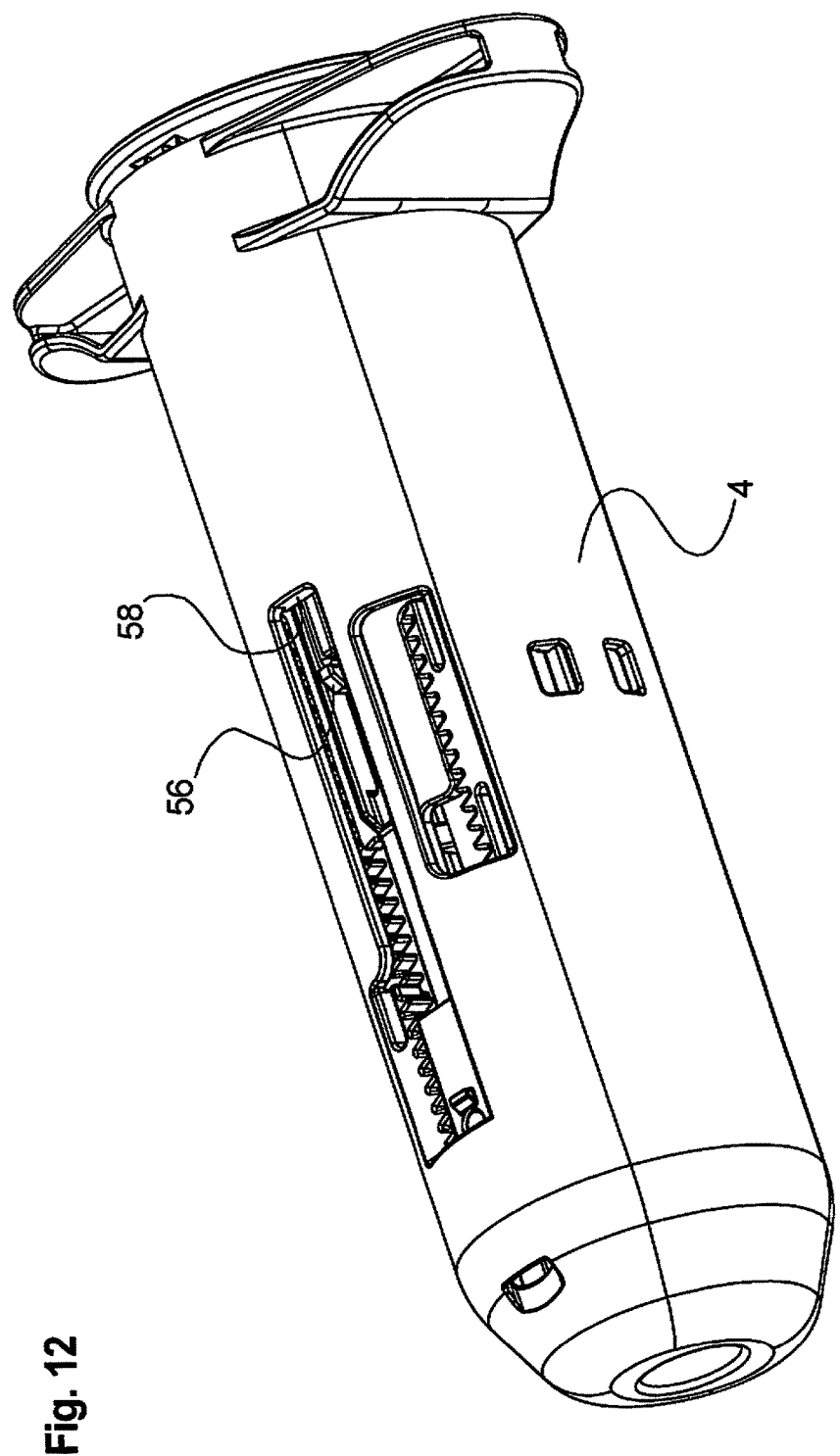
Figure 13:
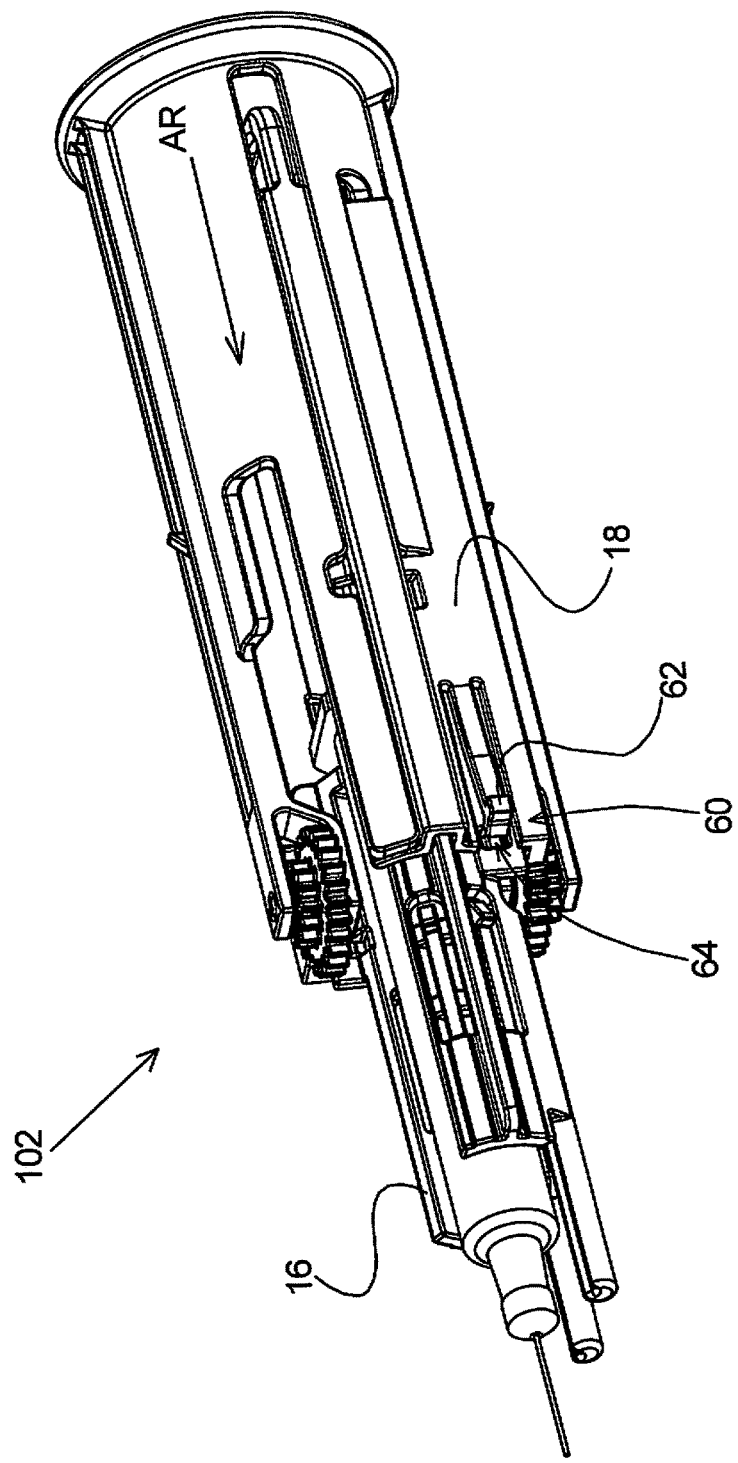
Figure 14:
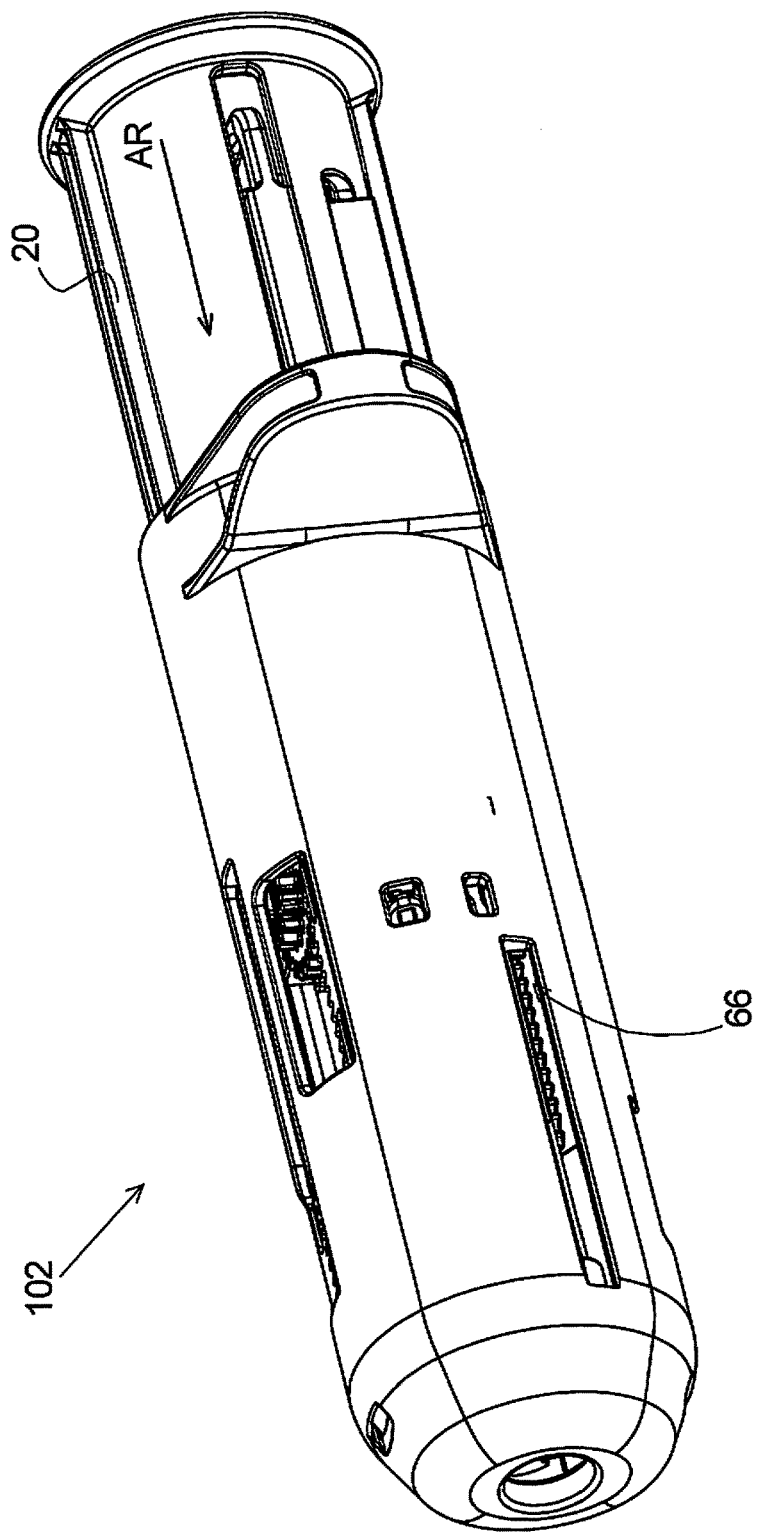
Figure 15:
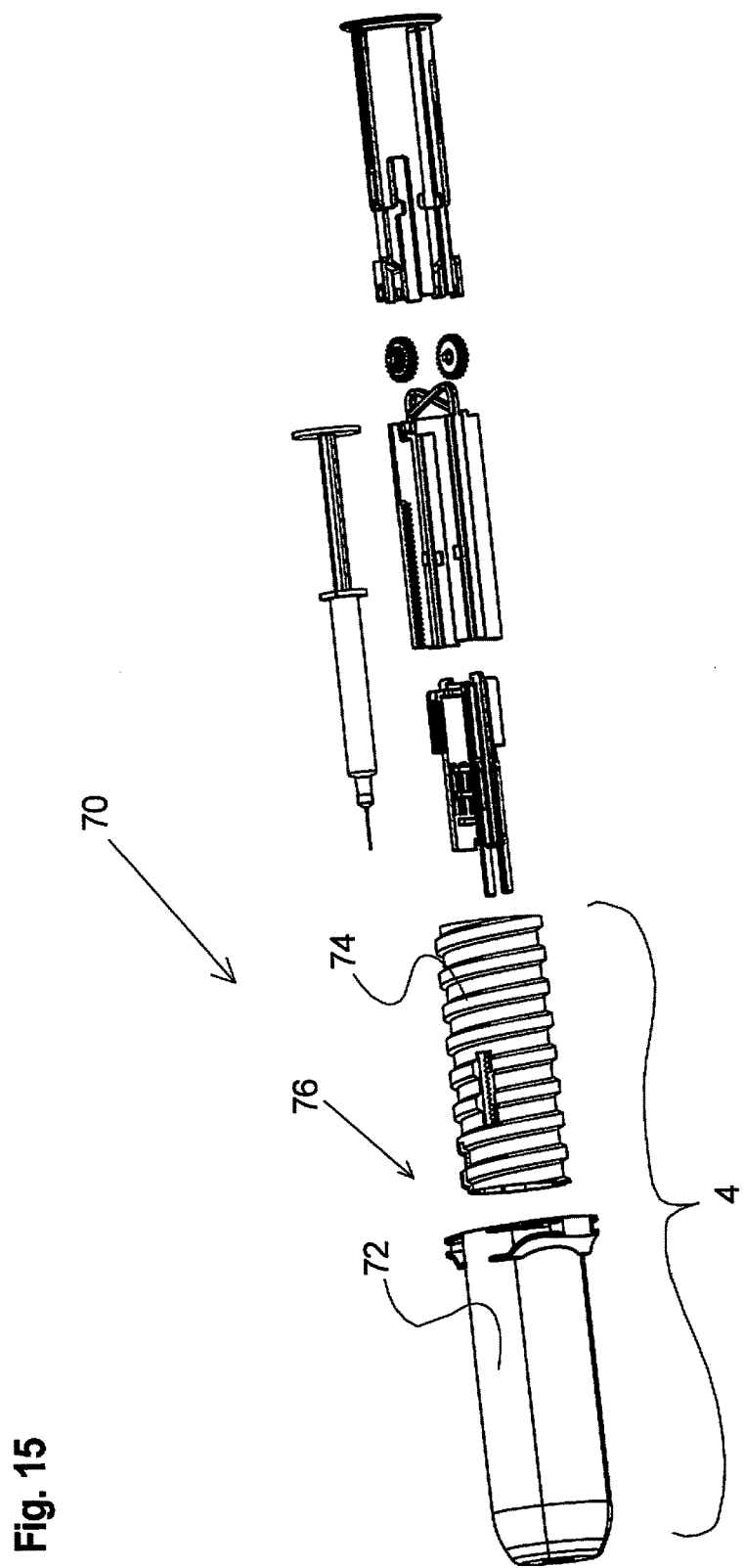
Figure 16:
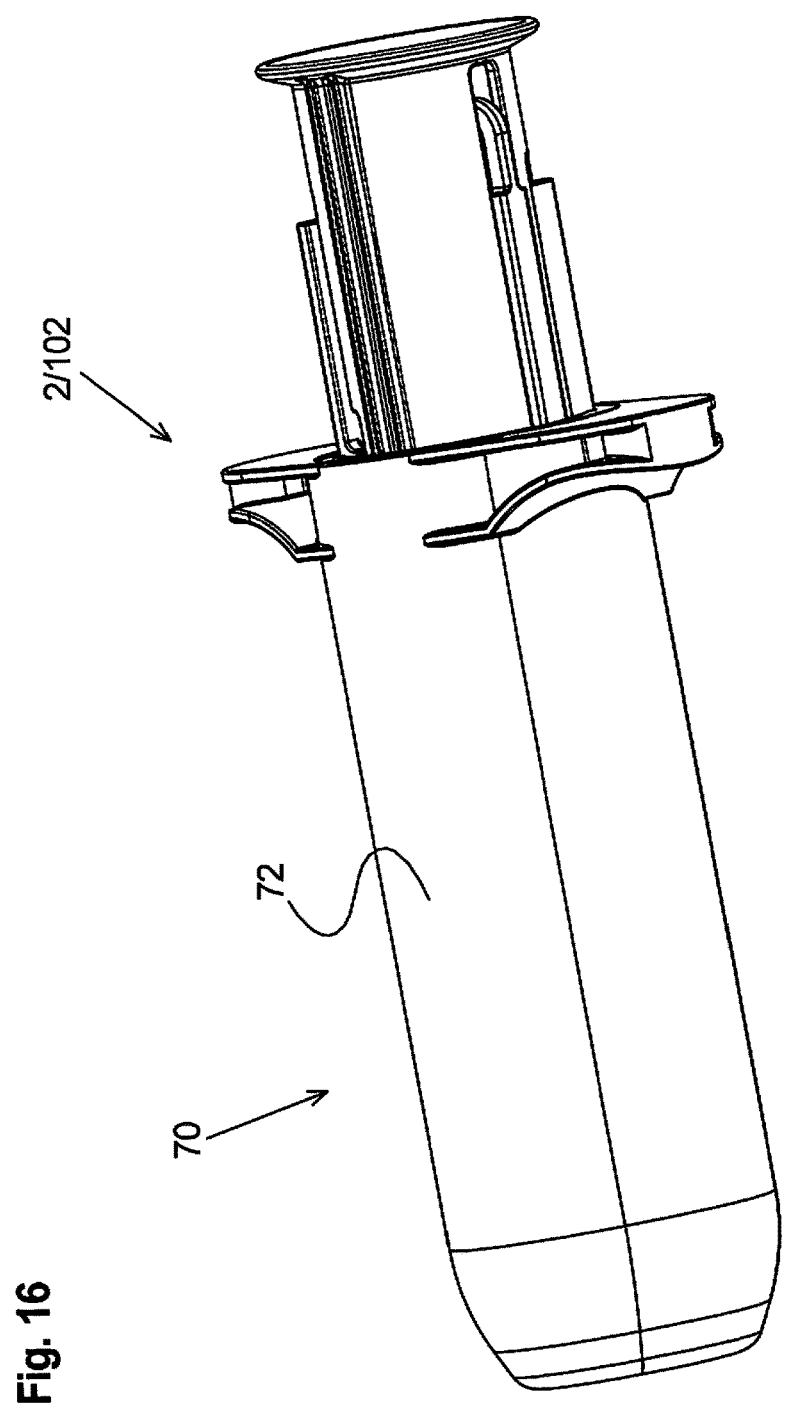
Figure 17:
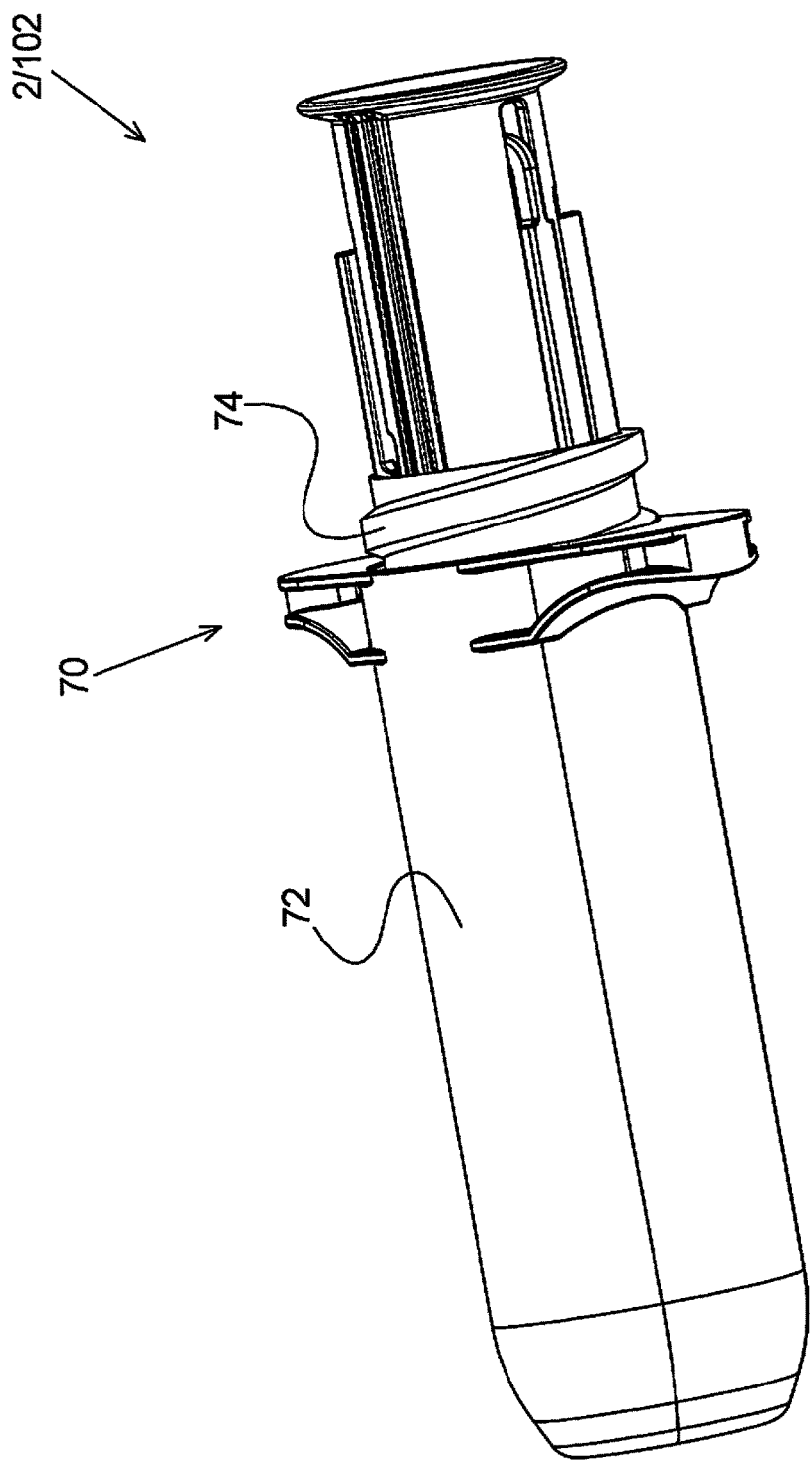
Figure 18:
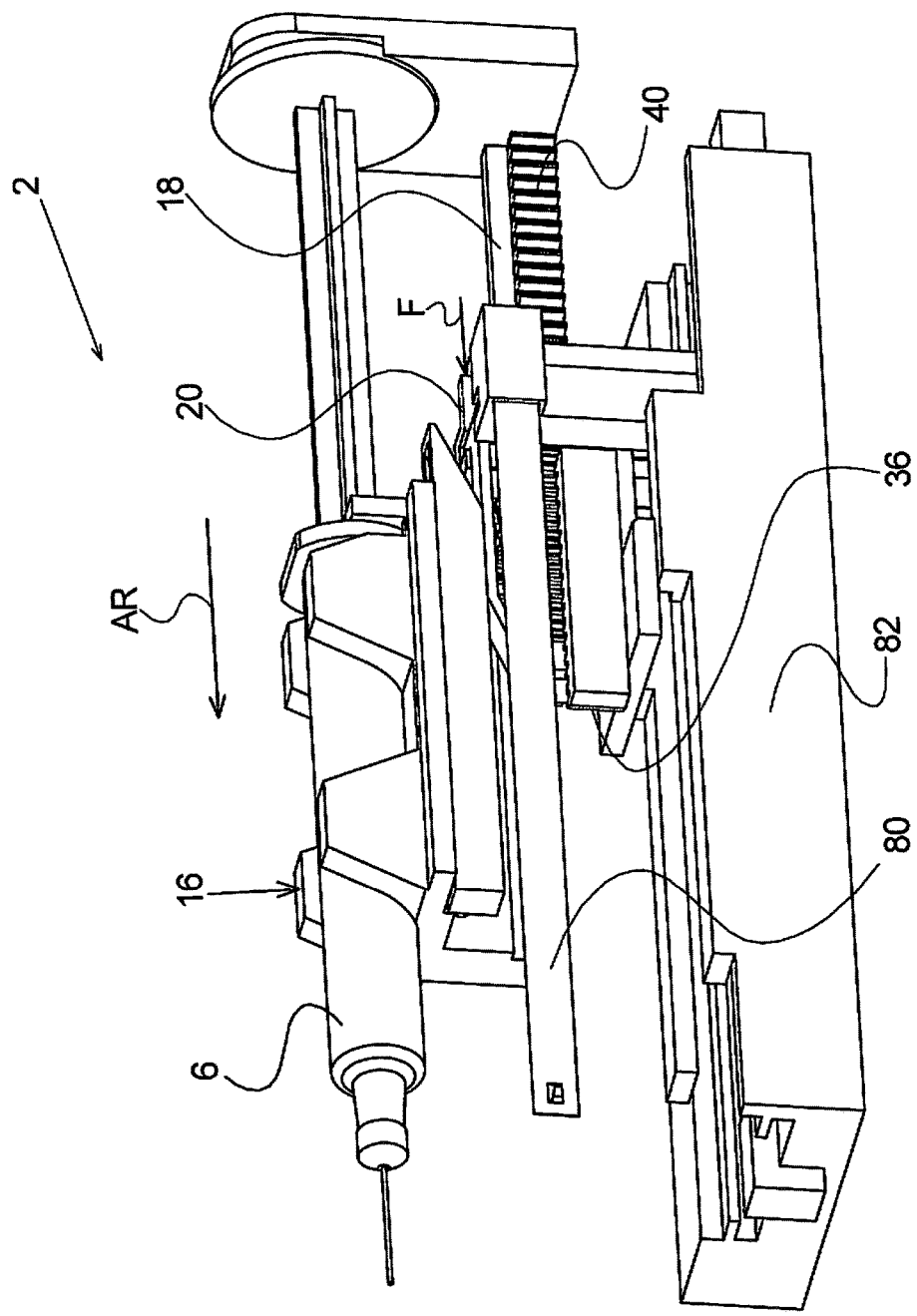

The figures illustrate an exemplary embodiment of the invention. The figures show:

FIG. 1, a perspective exploded view of an injection device according to the invention;

FIG. 2, a perspective view of the injection device in a starting position;

FIG. 3, a perspective view of a control arrangement of the injection device in the starting position;

FIG. 4, a perspective view of the injection device during a puncture stroke;

FIG. 5, a perspective view of the control arrangement during a puncture stroke;

FIG. 6, a perspective view of the control arrangement during an injection stroke;

FIG. 7, a perspective view of the control arrangement at the beginning of an empty stroke;

FIG. 8, a perspective view of the control arrangement during the empty stroke;

FIG. 9, a perspective view of the control arrangement at the beginning of a return stroke;

FIG. 10, a perspective view of the control arrangement during the return stroke;

FIG. 11, a perspective view of the control arrangement in an end position;

FIG. 12, a perspective view of the injection device in an end position;

FIG. 13, a perspective view of a control arrangement of an alternative embodiment of the injection device in a starting position;

FIG. 14, a perspective view of the alternative embodiment of the injection device in the starting position;

FIG. 15, a perspective exploded view of the injection device according to FIG. 1 comprising a puncture depth setting mechanism;

FIG. 16; a perspective view of the puncture depth setting mechanism according to FIG. 15 in a first setting position;

FIG. 17; a perspective view of the puncture depth setting mechanism according to FIG. 15 in a second setting position and FIG. 18, a perspective view of a further alternative embodiment of the injection device comprising a mechanical force accumulator.

FIG. 1 shows the individual elements of an injection device 2 having a housing 4 in which a syringe 6 is securely received, comprising an injection needle 8, a receiving chamber 10, a piston 12 and a piston ram 14. For this purpose, a syringe holder 16, which can be secured on the receiving chamber 10, and a ram holder 18, which can be secured on the piston ram 14, are movably received in the housing 4. By means of two spring elements 19 provided on one end of the ram holder 18, a certain pretension can be created when installing the syringe 6, by means of which certain manufacturing tolerances or different fill levels can be compensated.

The syringe holder 16 and the ram holder 18 together with an actuation element 20, on which a drive force F can be externally applied, in particularly manually, and having an inner side 22 of the housing 4, form a control arrangement 24, by means of which the syringe 6 is actuated during an application procedure in order to administer a medication Me contained in the receiving chamber 10 in a controlled manner. Here the intended application procedure comprises a puncture stroke, during which the needle 8 is stabbed into a tissue of the respective patient, an injection stroke, during which the medication Me is injected, an empty stroke, during which an overpressure of the injected liquid can be dissipated, and a return stroke, through which the needle 8 is displaced back into the interior of the housing 4.

In order to carry out this application procedure in a controlled manner, the control arrangement 24 comprises a transmission mechanism 26, which is substantially formed by a toothed gearing 28, as can be seen for example in FIG. 2.

As can be seen in particular in FIG. 3, the toothed gearing 28 comprises two two-tier gear wheels 30 rotatably mounted on the actuation element 20, which each form a first actuation-element-side toothing 32 with a first number of teeth and a second actuation-element-side toothing 34 with a second number of teeth.

In a drive direction AR of the actuation element 20, these gear wheels 30 can be brought into meshing engagement with different mating toothings by the application procedure. These mating toothings are thus formed by a first housing-side toothing 36 and a second housing-side toothing 38, arranged spaced apart from the first housing-side toothing and on an opposite side of the inner side 22 of the housing 4, and by a ram-holder-side toothing 40 and a syringe-holder-side toothing 42. For easier presentation, the housing-side toothings 36, 38 are shown without the rest of the housing 4.

In order to more easily bring the gear wheels 30 into meshing engagement with the various mating toothings during an application procedure, the individual toothings can be formed as pointed toothings. It is also advantageous if the toothings are formed at least partially resilient, for example through spring sections 44 illustrated on the ends of the housing-side toothings 36, 38. Alternatively or in addition, the mating toothings comprise increasing tooth heights in drive direction R, on the ends at which the gear wheels 30 come into meshing engagement, as can be seen for example in FIG. 5.

The application procedure is described below using the figures, wherein reference will be made to only one of the gear wheels 30.

In order to administer the medication Me received in the receiving chamber 10, the injection device 2 is initially positioned with the end-face-side end of the housing 4 on the affected position of the body of the patient, at which the medication Me is to be injected. The activation of the injection device 2 then occurs through manual application of the drive force F on the actuation element 20, for example by a thumb of the patient (not illustrated).

FIGS. 2 and 3 show the injection device 2 in an operation-ready starting position, in which the application of the drive force F occurs. A spring tab 46, which is held elastically displaceable on the actuation element 20, abuts a stop 48 formed by a wall of the housing 4, which is illustrated, in particular in FIG. 2, by a dashed line. In this way, the spring tab 46 and the stop 48 form a blocking mechanism 50, by means of which a threshold value is defined that must be attained by the drive force F in drive direction AR in order to start the application procedure and/or the puncture stroke. When the threshold value is reached, the spring tab 46 is resiliently inwardly displaced, so that the actuation element 20 can be displaced in drive direction AR, in order to perform the puncture stroke.

Alternatively to the illustrated arrangement formed from spring tab 46 and stop 48, the blocking mechanism 50 can also be formed by any other known and suitable mechanism through which a corresponding threshold value of the drive force F can be defined, such as for example by an arrangement comprising a locking element that can be sheared off, having a locking element that can pivot against a spring force, comprising a switchable gear wheel interacting with the actuation element 20, etc. (not illustrated).

In order to be able to create this application of the drive force F to the actuation element 20, with as smooth as possible a drive movement with a suitable drive speed v in drive direction AR, at least one damping element can also be provided which interacts with the actuation element 20 and is directly or indirectly coupled to move therewith. The damping element can be formed, for example, by a rotation damper or by a linear damper. It is also possible to provide a plurality of linear and/or rotation dampers, which interact for example with the actuation element 20, the syringe holder 16 and/or the ram holder 20, in order to be able to separately set and equalise a displacement speed for the individual stroke phases of the application procedure (not illustrated). In each case, for this purpose, all known and suitable embodiments of linear and rotation damping can be used.

FIG. 4 and FIG. 5 show an injection device 2 during the puncture stroke. As can be seen, the first actuation-element-side toothing 32 is in meshing engagement with both the first housing-side toothing 36 and with the ram-holder-side toothing 40. In addition, the part of the gear wheel 30 forming the actuation-element-side toothing 32 is so wide and so positioned that while adjacent to the ram-holder-side toothing 40 it is simultaneously in meshing engagement with the syringe-holder-side toothing 42. In this way, during the puncture stroke, the syringe holder 16 is securely coupled to the ram holder 18 via the first actuation-element-side toothing 32.

For this purpose, the gear wheel 30 is displaceably held on a spring arm 52 which abuts the inner side 22 of the housing 4 during the puncture stroke and is pressed inwardly by same, such that the gear wheel 30 meshes both with the ram-holder-side toothing 40 and with the syringe-holder-side toothing 42.

Through the movement of the actuation element 20, the first actuation-side toothing 32 of the gear wheel 30 thus rolls on the first housing-side toothing 36 and so a resulting drive torque M around an axis A of the gear wheel 30 drives the syringe holder 16 and the ram holder 18 simultaneously in drive direction AR via the ram-holder-side toothing 40 and the syringe-holder-side toothing 42, as illustrated in particular in FIG. 5.

FIG. 6 shows the injection device 2 after completion of the puncture stroke, during the injection stroke. As can be seen in the figure, at this point in time the gear wheel 30 only still meshes with the first housing-side toothing 36 and the ram-holder-side toothing 40. Consequently, there is no longer a resultant transfer of force from the gear wheel 30 to the syringe holder 16 at this point in time.

For this purpose, a recess 53 is left in the housing 4, as can be seen in particular from FIG. 4, in which the spring arm 52 can resiliently return so far towards its original shape, that the gear wheel 30 only still meshes with the ram-holder-side toothing 40 and the first housing-side toothing 36. Thus the ram holder 18, with the piston ram 14 received therein, is displaced further in drive direction AR, while the syringe holder 16 remains in the attained puncture position with the syringe 6 held therein.

Alternatively to the illustrated pivotable bearing of the gear wheel 30, any other displacement for cutting the meshing engagement between gear wheel 30 and syringe-holder-side toothing 42 is conceivable, such as for example a bearing of the gear wheel 30 displaceable in the axial or radial direction (not illustrated).

It is also conceivable, in order to remove the coupling between syringe holder 16 and ram holder 18, to design not the gear wheel 30 but rather the syringe-holder-side toothing 42 to be displaceable (not illustrated).

In each case, during said injection stroke, the piston ram 14, and/or the syringe piston 12 connected therewith, is pressed into the receiving chamber 10 and thus the medication Me is injected into the patient via the injection needle 8.

At the end of said injection stroke, the gear wheel 30 moves out of meshing engagement with the first housing-side toothing 36, as illustrated in FIG. 7. This allows the gear wheel 30, which then meshes via the first actuation-element-side toothing 32 thereof with only the ram-holder-side toothing 40, to roll freely along same without any further force transfer, as illustrated in FIG. 8. In this phase of the application procedure an empty stroke is created, from which a dwell time results, during which the injection needle 8 remains in the skin of the patient after the injection has been completed, so that the overpressure built up by the injected medication Me can dissipate before the injection needle 8 is removed from the injection channel.

At the end of said empty stroke, the second actuation-element-side toothing 34 on the spring section 44 comes into meshing engagement with the second housing-side toothing 38, while the first actuation-element-side toothing 32 of the gear wheel 30 meshes again with the ram-holder-side toothing 40, as illustrated in FIG. 9.

Simultaneously, during the empty stroke, a coupling between the syringe holder 16 and the ram holder 18 is produced via a schematically illustrated coupling arrangement 54. The coupling can be formed by all known embodiments which are suitable for removably connecting both holders 16, 18, such as for example by a catch arrangement comprising a spring element engaging in a holder, or alternatively by a recreated simultaneous engagement of the gear wheel 30 in the ram-holder-side toothing 40 and the syringe-holder-side toothing 42 (not illustrated).

Since the second housing-side toothing 38 is formed opposite the first housing-side toothing 36 on the opposite side of the inner side 22 of the housing 4, in this phase the gear wheel 30 rotates in the opposite direction with respect to the puncture and injection strokes, wherein a torque M2 is generated about the axis A also in an oppositely orientated direction.

Through this reversal of the direction of rotation, the ram holder 18, which is still meshed with the gear wheel 30 via the ram-holder-side toothing 40, is displaced opposite to the drive direction AR of the actuation element 20 along a return direction RR, as illustrated in FIG. 10. Because of the connection between the ram holder 18 and the syringe holder 16 produced by the coupling arrangement 54, the syringe holder is also moved along the return direction RR.

Said return stroke ends in an end position, in which the actuation element 20 has moved to an end stop in the housing 4 and the injection needle 8 is again completely arranged inside the housing 4, as illustrated in FIGS. 11 and 12. The actuation element 20 can be locked in said end position in order to block it from being pulled out again from the housing 4. The locking employs, for example, a catch 56 which can abut a correspondingly positioned catch stop 58 of the housing 4.

In said end position, the injection device 2 can thus be disposed of after the one-off use thereof, wherein it is ensured that the injection needle 8 cannot protrude from the housing 4.

FIGS. 13 and 14 show an alternative embodiment of the injection device 102 which is also used to perform an application procedure comprising a puncture stroke, an injection stroke, a dwell time and a return stroke. The alternative injection device 102 has a construction corresponding with the above described injection device 2, so that all corresponding elements of the alternative injection device 102 are identified with reference signs corresponding with the injection device 2.

The alternative injection device 102 essentially differs from the injection device 2 in that no syringe-holder-side toothing 42 is provided on the syringe holder 16. Instead, a connection means 60 is provided for detachable motion-coupling of the syringe holder 16 with the ram holder 18 during performance of the puncture stroke, which comprises for example an engagement element 62 resiliently held on the ram holder 18, which on assembly of the injection device 102 is pressed into a form-fitting engagement with a holder 64 inserted in the syringe holder 16, wherein said engagement position in the starting position of the injection device 102 and during the puncture stroke is ensured by the inner side 22 of the housing 4.

After completion of the puncture stroke, the engagement element 62 which presses outwardly against the inner side 22 due to the resilient return force is, however, arranged at the height of a recess 66 of the housing 4, as can be seen in FIG. 14, so as to be detachable from the form-fitting engagement with the syringe holder 16. In this way, the ram holder 18 can now again be displaced relative to the syringe shoulder 16 in drive direction AR, in order to carry out the injection stroke.

Alternatively to the connection means 60 illustrated here, the coupling between the syringe holder 16 and the ram holder 18 of the injection device 102 can also be produced through any other known and suitable embodiment of the connection means 60, for example through the use of a displaceable sliding block, a locking element that can be sheared off or a switchable freewheel (not illustrated).

FIG. 15 further shows a puncture depth setting mechanism 70 which can be used for the injection device 2; 102, which substantially consists of a two-part housing 4. Said housing comprises a first end-face-side housing part 72, which can be displaced relative to a second housing part 74 in order to set a desired puncture depth. For this purpose, for example an adjustable screw connection 76 is provided between the two housing parts 72, 74, as illustrated.

By means of the screw connection 76, the injection device 2; 102 can be brought into a setting according to FIG. 17, relative to a setting for a maximum puncture depth according to FIG. 16, in which the end-face-side first housing part 72, which during the injection procedure acts as a stop on the encountered body part of the patient, is brought further forward so that during the puncture stroke the injection needle 8 can be displaced less far out of the housing 4.

Alternatively to the illustrated embodiment of the puncture depth setting mechanism 70, any other embodiment can be used, by means of which the first housing part 72 can be positioned in different positions with respect to the second housing part 74. For example the first housing part 72 can be moved laterally or along a control cam with respect to the second housing part, or can be displaced into various predetermined positions by means of a displaceable actuation element (not illustrated). In a further alternative embodiment of the puncture depth setting mechanism 70, a removable spacer can also be used, which can be exchanged with another spacer having different longitudinal dimensions in order to secure a specified puncture depth (not illustrated).

FIG. 18 shows an automatically operable embodiment of the injection device 2, in which the application of a drive force F to the actuation element 20 is achieved by means of a mechanical force accumulator 80. The actuation element 20 is formed here, for example, by a gear wheel holder engaged by a scroll spring as a mechanical force accumulator 80, which is held on a support 82 of the injection device 2, which is not illustrated in more detail.

In addition, the syringe holder 16 is so designed that, after an application, the syringe 6 can be exchanged for a new syringe 6 in order that the injection device 2 may be used multiple time.

The invention claimed is:

1. An injection device comprising:
   a housing;
   a syringe including an injection needle, a receiving chamber, a piston and a piston ram operatively mounted within said housing;
   a syringe holder, said syringe holder being movable relative to the housing and on which the receiving chamber is secured, the syringe insertable into the syringe holder;
   a control arrangement for controlled actuation of the syringe during an application procedure that includes at least one puncture stroke, one injection stroke and one return stroke;
   said control arrangement including an actuation element for applying a drive force to the syringe holder;
   a ram holder movable relative to the housing and on which the piston ram is secured; and
   a transmission mechanism for coupling the ram holder to the actuation element,
   wherein the transmission mechanism comprises a toothed gearing, and wherein the ram holder is driven depending on a relative movement of the actuation element with respect to the housing, said toothed gearing including a row of toothing formed on the housing for driving the ram holder.

2. The injection device according to claim 1, wherein the toothed gearing comprises an actuation-element-side toothing, which, in the drive direction of the actuation element, is brought into meshing engagement with a first housing-side toothing thus generating a first direction of rotation and, spaced apart therefrom, with a second housing-side toothing arranged on another side of the housing thus generating a second direction of rotation, wherein the second direction of rotation is orientated opposite to the first direction of rotation.

3. The injection device according to claim 2, wherein the actuation-element-side toothing and the first housing-side toothing and the second housing-side toothing are at least partially formed as pointed teeth and are at least partially resiliently formed and the first housing-side toothing and second housing-side toothing have tooth heights increasing with respect to the drive direction, at least in some regions.

4. The injection device according to claim 1, wherein the toothed gearing comprises a gearwheel rotatably mounted on the actuation element, which is brought into meshing engagement both with the toothing formed on the housing and with a toothing formed on the ram holder.

5. The injection device according to claim 4, wherein the gearwheel is brought into meshing engagement with a syringe-holder-side toothing.

6. The injection device according to claim 4, wherein at least one second actuation-element-side toothing is provided on the gearwheel in addition to a first actuation-element-side toothing, and the first actuation-element-side toothing comprises a first number of teeth and the second actuation-element-side toothing comprises a second number of teeth which is different from the first number of teeth and in the drive direction of the actuation elements, both actuation-element-side toothings are brought into meshing engagement with mating toothings, thus generating a rotary movement with different gearing ratios.

7. The injection device according to claim 6, wherein the second actuation-element-side toothing of the gearwheel is brought into meshing engagement with second mating toothing which is formed by second housing-side toothing, in order to perform the return stroke, and
   the first actuation-element-side toothing of the gearwheel is simultaneously brought into meshing engagement with the ram-holder-side toothing,
   wherein the syringe holder is firmly coupled with the ram holder and the coupling is produced by means of a spring element removably engaged in a holder.

8. The injection device according to claim 1, wherein spring elements are provided on the ram holder, for applying a pretension to the piston ram in the drive direction.

9. The injection device according to claim 1, wherein at least one damping element is provided interacting with the actuation element.

10. The injection device according to claim 1, wherein a blocking mechanism is provided, by means of which the actuation element is blocked in a starting position until a threshold value of a drive force acting in the drive direction is attained.

11. The injection device according to claim 10, wherein the blocking mechanism comprises a spring tab that abuts against a stop and comprises a locking element that pivots against a spring force.

12. The injection device according to claim 1, wherein the syringe holder is securely coupled to the ram holder in order to perform a puncture stroke.

13. The injection device according to claim 12, wherein the coupling is produced by means of an engagement element detachably engaged in a holder or by means of a displaceable sliding block.

14. The injection device according to claim 1, wherein the toothed gearing is provided with an empty stroke to produce a dwell time, by means of which, despite the relative movement of the actuation element relative to the housing, no drive force is transferred to the ram holder.

15. The injection device according to claim 1, wherein the actuation element is locked in an end position in which the return stroke is completed and the needle is again completely arranged inside the housing.

16. The injection device according to claim 1, wherein the housing comprises an end-face-side housing part which is displaceable with respect to the rest of the housing in order to set a puncture depth.

17. The injection device according to claim 1, wherein the actuation element is acted on by the drive force via a mechanical force accumulator.

* * * * *